United States Patent [19]

Markham

[11] Patent Number: 5,070,085

[45] Date of Patent: *Dec. 3, 1991

[54] COMPOSITIONS AND METHODS FOR ADMINISTERING THERAPEUTICALLY ACTIVE COMPOUNDS

[75] Inventor: Richard G. Markham, Prescott, Ariz.

[73] Assignee: Oxycal Laboratories, Inc., Prescott, Ariz.

[*] Notice: The portion of the term of this patent subsequent to Apr. 18, 2006 has been disclaimed.

[21] Appl. No.: 459,806

[22] PCT Filed: Sep. 15, 1989

[86] PCT No: PCT/US89/04046

§ 371 Date: Apr. 6, 1990

§ 102(e) Date: Apr. 6, 1990

Related U.S. Application Data

[63] Continuation-in-part of Ser. No. 246,504, Sep. 19, 1988, Pat. No. 4,968,716, which is a continuation-in-part of Ser. No. 36,598, Apr. 10, 1987, Pat. No. 4,822,816.

[51] Int. Cl.$^5$ .................... A61K 31/62; A61K 31/60; A61K 31/34; A61K 47/00

[52] U.S. Cl. .................. 514/161; 514/226.5; 514/165; 514/474; 514/784; 514/785; 514/777; 514/946

[58] Field of Search ............ 514/165, 226.5, 473, 514/946, 161, 784, 785, 77

[56] References Cited

U.S. PATENT DOCUMENTS

| | | | |
|---|---|---|---|
| 2,606,903 | 8/1952 | Ruskin | 424/10 |
| 2,822,317 | 2/1958 | Gulesich et al. | 514/474 |
| 4,324,778 | 4/1982 | Davis | 424/10 |
| 4,822,816 | 4/1989 | Markham | 514/474 |
| 4,968,716 | 11/1990 | Markham | 514/474 |

OTHER PUBLICATIONS

Lewin, S. "Vitamin C: *Its Molecular Biology and Medical Potential*" *(1976) pp. 12–13.*

Thomas et al., Chem. Toxic. vol. 21 (4) pp. 449–52 (1983).

Morrison and Boyd—*Organic Chemistry*, 3rd edition, copyright 1973 (N. Y. University, Allyn and Bacon Inc.) p. 1075, Table 34.1.

*Primary Examiner*—Frederick E. Waddell
*Assistant Examiner*—Raymond J. Henley, III.
*Attorney, Agent, or Firm*—Fulwider, Patton, Lee & Utecht

[57] ABSTRACT

A composition useful for administering therapeutically active compounds to improve the body absorption and/or retention thereof comprising a composition includes a therapeutically active compound having a molecular weight below about 5,000, having an acidic functional group and a pKa of $\leq 6$ at pH 7.4 normally eliminated unmetabolized from the body via the renal tubular secretion pathway for organic anions, for example, Vitamin C, and at least one compound selected from the class consisting of L-threonic, L-xylonic and L-lyxonic acids, and the edible salts, aldono-lactones and aldono-lactides thereof.

A method for establishing and maintaining body levels of a therapeutically active compound includes the step of administering a therapeutically effective dose of this composition.

19 Claims, 3 Drawing Sheets

COMPOSITIONS AND METHODS FOR ADMINISTERING THERAPEUTICALLY ACTIVE COMPOUNDS

This application is a continuation-in-part of U.S. application Ser. No. 246,504, filed Sept. 19, 1988 (now issued U.S. Pat. No. 4,968,716, issued Nov. 6, 1990), which was, in turn, a continuation-in-part of U.S. application Ser. No. 07/036,598, filed Apr. 10, 1987 (now issued U.S. Pat. No. 4,822,816, issed Apr. 18, 1989).

This invention relates to new compositions of matter and methods of use thereof.

More specifically, the invention concerns a composition for improving the effectiveness of certain therapeutically active compounds.

In a further respect, the invention concerns methods for establishing and maintaining therapeutically effective levels of such compounds in the body.

In a more particular respect, the invention relates to improved compositions of therapeutically active compounds such as antibiotics, vitamins, amino acids, anti-inflammatory's, analgesics, anti-pyretics, and the like, and methods of use thereof.

Even more specifically, the invention relates to an improved composition containing Vitamin C and methods of use thereof.

In preventive or remedial drug therapy it is generally desired to establish an initial, physiologically effective level of a drug or other therapeutically active compound in the human or animal host body and then maintain that effective level for an extended period of time, as required to effect the desired physiological result. An improvement in either the absorption ("uptake") rate or retention (decrease in the excretion rate) or both generally yields important physiologic and therapeutic advantages. It is also highly advantageous if unwanted side effects of the therapeutically active compound can be reduced or eliminated.

In order to initially illustrate the practices and principles of the invention to those skilled in the art, the invention will now be described by reference to the use of the invention in the improvement of Vitamin C therapy. However, it is to be clearly understood that the invention is not limited to its application in this field, as will appear more fully below.

Prior workers have identified over 300 separate metabolic mechanisms in which Vitamin C is involved in physiologic reactions. These mechanisms range from the antiscorbutic effect first observed by Dr. Robert Lind in 1740 to more recently discovered anti-oxidant free-radical scavenging reactions, to co-reaction with enzymes in the formation of collagen, energy metabolism accentuation in the polynuclear-leucocytes and facilitation of iron absorption.

The clinical effects of such metabolic reactions have been widely recognized and reported. For example, the free-radical scavenging effect is believed to enable the body to convert carcinogens to non-toxic derivatives which are eliminated in the uring and, consequently, to ameliorate the effects of smoking and exposure to other environmental pollutants and temperature extremes. Animal studies have demonstrated that body enzymes convert ascorbates to oxidation products which have demonstrated tumor growth inhibition.

Consequently, there is little scientific doubt that the establishment and maintenance of effective levels of Vitamin C and its derivatives in the human body yield important health advantages. The presence of Vitamin C in substantial concentration has been observed in the adrenals, ovaries, brain, pituitaries, liver spleen, blood cells, blood serum, and extra-cellular lung liquids.

Most animals have a liver enzyme which enables them to actually manufacture Vitamin C in situ by conversion of blood sugar into ascorbic acid. However, humans do not have this enzyme. As a consequence, the Vitamin C which is required by the human body for the various metabolic reactions discussed above must be ingested with the human diet. Furthermore, the human body does not have the ability to store Vitamin C . If unmetabolized, it is excreted. Low levels of Vitamin C and its derivatives in the human body produce a variety of undesirable physiological responses and extremely low levels produce extreme responses which may result in death, e.g., from scurvy. Wholly apart from these "normal" requirements of Vitamin C, it is important in some therapeutic modalities to establish and maintain above-normal Vitamin C levels in the body. These above-normal concentrations are difficult to establish and maintain because the human body exhibits only a finite tolerance for Vitamin C (ascorbic acid) with resultant diarrhea and other side reactions, such as gastric irritation and inflammation if these tolerances are exceeded.

I have now discovered compositions and methods for improving the effectiveness, i.e. establishment and/or maintenance of body levels of therapeutically active compounds which are normally eliminated from the body without metabolism via the renal tubular secretion pathway for organic anions. Such therapeutically active compounds have a molecular weight below about 5,000, have an acidic functional group and a pKa of 6 at physiological pH=7.4. The compositions of the invention comprise such therapeutically active compounds and at least one compound selected from the class consisting of L-threonic, L-xylonic and L-lyxonic acids, and the non-toxic edible salts, aldono-lactones and aldono-lactides thereof.

In the preferred embodiment of the methods of the invention, the method which I have discovered includes the step of administering a physiologically effective dose of this composition to a human or animal subject.

According to an alternative method, the aldonic compound is administered in a first step to establish an effective level thereof in the body and, thereafter, the therapeutically active compound is administered.

More particularly, I have now discovered compositions and methods for improving the establishment and maintenance of high levels of Vitamin C (including its derivatives) in the human body. Briefly, according to this embodiment of the invention, the composition which I have discovered comprises a compound having Vitamin C activity and at least one compound selected from the class consisting of L-threonic, L-xylonic and L-lyxonic acids, and the edible salts, aldono-lactones and aldono-lactides thereof.

In another preferred embodiment, the method which I have discovered for establishing Vitamin C levels in the human body includes the step of administering this composition to a subject.

As used herein, the term "compound having Vitamin C activity" means Vitamin C (L-ascorbic acid) and any derivatives thereof which exhibit antiscorbutic activity. Such derivatives includes, for example, oxidation products, such as dehydroascorbic acid and edible salts of ascorbic acid such as, illustratively, calcium sodium, magnesium, potassium and zinc ascorbates, esters of Vitamin C with organic and inorganic acids, e.g., L-Ascorbic Acid 2-0-sulfate, L-Ascorbic Acid 2-0-phosphate, L-Ascorbic Acid 3-0-phosphate, L-Ascorbic Acid 6-hexadecanoate, L-Ascorbic Acid monostearate, L-Ascorbic Acid dipalmitate, and the like.

Metabolites of ascorbic acid and its derivatives include the aldonic acids, aldono-lactones, aldono-lactides and edible salts of aldonic acids. As will appear, the compositions of the present invention are characterized by the presence of at least one or more of these metabolites corresponding, to three specific aldonic acids: L-threonic acid, L-xylonic acid and L-lyxonic acid.

The aldono-lactones have the structural formula wherein R is hydrogen or —CH—OH and n=1 to 3.

The presence of one or more of these metabolites in the compositions of the invention is both a convenient way of identifying such compositions and is also necessary to achieve the desired result, improvement in absorption and/or retention of the Vitamin C or other therapeutically active compound.

A suitable method for preparing the improved Vitamin C composition of the invention comprises heating L-ascorbic acid with a non-toxic metal compound, e.g., calcium carbonate, sodium bicarbonate, and the like, under oxidizing conditions at an elevated temperature, e.g., 40° C.-89° C., to convert a substantial proportion of the ascorbic acid to its corresponding salt, e.g., calcium or sodium ascorbate and drying the reaction mixture to produce a solid product of essentially neutral pH (e.g., 6.0-7.5). Preferably a slight stoichiometric excess of the metal salt reactant is provided. The resultant product has an iodine ascorbate assay in the range 50-480 mg./500 mg. sample depending upon process parameters, with the higher ascorbate activity preferred for practical reasons. Longer heating at oxidizing conditions produces lower iodine ascorbate assays.

The compositions of the invention appear useful in administering Vitamin C to patients who have low ascorbic acid tolerance. In particular, patients who have a tendency to form kidney stones are particularly susceptible to difficulties when ingesting ascorbic acid and its common derivative, calcium ascorbate, which cause elevated urine oxalate levels. there are indications that the compositions of the present invention can be administered without increasing the oxalate level in the urine to the levels encountered when the prior art compositions and methods are used. These compositions are especially suitable as a means of establishing and maintaining adequate ascorbate body levels in such kidney stone-prone subjects. The Vitamin C compositions of the invention are also useful in the treatment of inflammatory diseases, such as arthritis.

The effectiveness of the aldonic compounds in improving the absorption, tolerance and/or retention rates of Vitamin C compounds is also generally applicable to the improvement of such characteristics of therapeutically active compounds which have a molecular weight below about 5,000, which have an acidic functional group and pKa≦6. The physiological mechanisms responsible for these improvements appear to be the inhibition of normal elimination of such unmetabolized therapeutically active compounds from the body via the renal tubular secretion pathway for organic anions and the improved absorption of these components through the cell walls of body tissue. The aldonic compounds apparently act to provide both the improved absorption and inhibited renal excretion effect. A general description of the various renal secretion pathways is contained in the article by Hirsch and Hook, *Journal of Pharmacology and Experimental Therapeutics* [Vol. 171, p. 103 (1970)].

The amount of the aldonic compound which is required in the compositions of the invention is a therapeutically effective proportion. The exact proportion will vary somewhat depending on the exact nature of the therapeutically active compound and other factors which will occur to those skilled in the art. In general, the reduced kidney secretion rate and/or increased body absorption rate is improved somewhat by even very minor amounts of the aldonic compounds. These characteristics will be improved by increasing the proportions of the aldonic compound and the upper limit is established by practical considerations such as avoiding undue dilution of the therapeutically active ingredient to the point that an adequate minimum dosage is not administered. According to the best present information, the proportion of the aldonic compound in the compositions of the invention can vary from less than 1 wt. % to 24 wt. %. Practical therapeutic effects have been observed at concentrations of the aldonic compound in the rage of 0.10 wt. % and the presently preferred range is about 1 wt. % to about 7 wt. % of the aldonic compound.

The compositions of the invention can be prepared by simply physically admixing the components of the compositions. Alternatively, in the case of Vitamin C, compositions can be prepared in situ by the techniques illustrated in the working examples.

Representative, non-limiting examples of such therapeutically active compounds which can be improved in accordance with the invention, include compounds having a pKa≦6 and having acidic functional groups such as carboxylic groups, ene-diol groups, phenolic groups and the like. Such compounds are of widely diverse structure and pharmaceutical utility, and, for example, include:

| USAN (U.S. Adopted Name) | pKa | Pharmaceutical Activity |
|---|---|---|
| Ascorbic Acid | 4.17 | Vitamin |
| Prioxicam | 5.1 | Anti-Inflammatory |
| Warfarin Potassium | 5.05 | Anticoagulant |
| Ampicillin | 3.3 | Antibiotic |
| Aspirin | 3.5 | Anti Inflammatory |
| Carbenicillin | 2.6 | Antibiotic |
| Mezlocillin | 2.7 | Anti-bacterial |
| Salsalate | 3.5 | Analgesic |
| Niacin | 4.85 | Vitamin |
| Penicillin G. Potassium | 2.76 | Anti-bacterial |
| Oxacillin Sodium | 2.84 | Anti-Inflammatory |
| Arginine | 3.2 | Amino Acid |
| Sulindac | 4.7 | Anti-Inflammatory |
| Dinoprost | 4.9 | Oxytocic |
| Suprofen | 3.9 | Anti-Inflammatory |
| Ethacryaic Acid | 3.5 | Diuretic |
| Fenoprofen | 4.5 | Analgesic |
| Pantothenic Acid | 3.5 | Vitamin |
| Furosemide | 3.9 | Diuretic |
| Indomethacin | 4.5 | Anti-Inflammatory |
| Fusic Acid | 5.35 | Anti-bacterial |
| Meclofenamic Acid | 4.0 | Anti-Inflammatory |
| Tolmetin | 3.5 | Anti-Inflammatory |
| Benoxaprofen | 3.5 | Anti-Inflammatory |

| USAN (U.S. Adopted Name) | pKa | Pharmaceutical Activity |
|---|---|---|
| Valproic Acid | 4.8 | Anti-Convulsant |
| Sulfisoxazole | 5.0 | Anti-bacterial |
| Alclofenac | 4.6 | Anti-Inflammatory |
| Tryptophan | 2.9 | Amino Acid |
| Biotin | 3.5 | Vitamin |
| Captropril | 3.7 | Anti-hypertensive |
| Ornithine | 3.5 | Amino Acid |
| Cefoxitin | 2.2 | Anti-bacterial |
| Bumetanide | 4.0 | Diuretic |
| Tolazamide | 3.1 | Anti-diabetic |
| Cloxacillin Sodium | 2.7 | Amino Acid |
| Cefoperazone | 2.55 | Anti-bacterial |
| Tyrosine | 2.8 | Amino Acid |
| Indomethacin Sodium | 4.5 | Anti-Inflammatory |

Therapeutically active compounds of the type described above, which are suitable for use in practicing the invention can be readily selected and identified by routine tests by those skilled in the art. Determination of whether a particular compound is excreted unmetabolized can be made by urinalysis. The selection can be further confirmed by the smooth muscle tests described in Example 14 and the animal studies described in Examples 12 and 13.

The following examples are presented for purposes of illustrating the practice of the invention and are not intended as limitations on the scope thereof.

EXAMPLE 1

To an 80-gallon, steam-heated stainless steel reaction vessel was added 60 lbs. of hot (44° C.) water. Ascorbic acid-U.S.P., 110.23 lbs, was added in one portion to the hot water. The resulting slurry was mechanically stirred and heated with steam (pressure 15 p.s.i.) until a temperature of 70° was achieved.

To the aqueous slurry of ascorbic acid was added 23 lbs. of calcium carbonate. The incremental addition of the carbonate required 3–4 minutes The reaction mixture appeared gray in color and much foaming due to the evolution of $CO_2$ was evident. After eight minutes of stirring, most of the foaming had subsided and the reaction mixture appeared red-brown in color. The solution temperature was 80° C. Stirring and heating were continued for 15 minutes until the temperature of the reaction mixture reached 98° C. where it was maintained for an additional 20 minutes, after which an additional 8.25 lbs. of calcium carbonate was added, with stirring. After foaming ceased, the reaction mixture was then pumped to a double-drum steam-heated dryer (surface temperature approximately 250° F.) The pumping-drying step required 35 minutes. The dried product was light-tan color and the yield was approximately 120 pounds of product.

Optionally, air can be bubbled through the reaction mixture to promote the reaction of the ascorbic acid.

Assays were performed immediately on 5.00 g. samples dissolved in 500 ml. distilled water.

The material collected during the drying process showed 400 mg. anhydrous calcium ascorbate per 500 mg. by the standard iodine titration technique. The same aqueous solution showed pH 7.0.

EXAMPLE 2

The following example describes clinical tests comparing the product of Example 1 (test material) with L-ascorbic acid and citric acid (placebo), measuring intra-cellular and serum ascorbate levels, urinary ascorbate output and urinary oxalate excretion at various times after ingestion of standard doses of the test L-ascorbic acid and placebo.

SUMMARY OF THE PROTOCOL

Twelve men, ages 27 to 45, were studied.

All were instructed that they should be on a low Vitamin C diet for one week prior to the study (no citrus products and no large amounts of green leafy vegetables).

Following overnight fast, blood and 24-hour urine samples were taken. White blood cell and 24-hour urinary ascorbate and oxalate levels were determined and correlated with serum ascorbate levels The 12 men were divided into three groups, and were given the following supplements:

(a) Test Group: 4000 MG* per day of the product Ex. 1

*4000 MG is equivalent in ascorbate (iodine test) to 3000 MG L-ascorbic acid.

(b) Ascorbate Group: 3000 MG of L-ascorbic per day.

(c) Citric Acid Group: 3000 MG of citric acid per day.

All 12 continued on a low Vitamin C diet Blood samples were taken at 0, 4, 8 and 24 hours after morning ingestion of the designated supplements Urinary 24-hour ascorbate and oxalate levels were determined.

After a wash-out period (varying from two days to several days, due to job situation of participants), the groups were switched to another supplement, as follows:

(a) Test group to citrate group.

(b) Citrate group to ascorbate group.

(c) Ascorbate group to test group.

Supplements were taken at the same level (4000 MG of Ex. 1 product, 3000 MG of L-ascorbic and 3000 MG of citric acid) by all three groups. Blood samples were again drawn at 0, 4, 8 and 24 hours from time of ingestion. A 24-hour urine was also collected by all 12 participants at the end of the period. Again, all specimens were analyzed for their respective concentration of ascorbate and oxalate levels.

ANALYTICAL PROCEDURES

The analytical procedures utilized are described in: *Clinical Chemistry, Principles and Techniques,* edited by Richard J. Henry, Donald D. Cannon and James W. Windelman, Harper and Row, 1974 p. 1393–1398.

*Standard Method of Clinical Chemistry,* J. S. Roe, edited by Seligson D. New York, Academic Press, 1961, Vo. 3, p. 35.

In the quantitation of 24-hour urine oxalate, an aliquot of urine is shaken with an adsorbent which selectively binds the oxalate. The extracted urine is discarded and the oxalate is eluted from the adsorbent with dilute alkali.

Oxalate is oxidized to hydrogen peroxide and carbon dioxide by oxalate oxidase. The hydrogen peroxide reacts with 3-methyl-2-benzothiozolinone hydrazone (MBTH) and 3 (dimethylamino) benzoic acid (DMAB) in the presence of peroxidase to yield an indamine dye with a maximum absorbance at 590 NM.

The urine oxalate test is further described in the following references:

Hodgekinson, A.: *Oxalic Acid in Voilogy and Medicine,* Academic Press, New York, 1977.

Robertson, W. D.; Chrystowski, G. A.: *Urinary Oxalate Excretion by Main Following Ascorbine Acid Ingestion.* Prog. Soc. Exp. Bil. Med. 85:190, 1954.

Costello, J.: *The Effect of Ascorbic Acid on Oxalate Metabolism in Human Biochemistry and Clinical Pathology,* edited by G. A. Rose, W. G. Robertson and R. W. E. Watts. proceedings of an International Meeting in London, 1971, pp. 270-273.

The results of this clinical study are set forth below:

TABLE 1

| | Percent Change* in Group | | |
|---|---|---|---|
| | Citrate | L-ascorbic | Test |
| Serum Ascorbate Level | | | |
| 4th Hour | 10 | 180.3 | 264.8 |
| 8th Hour | 19.6 | 91.6 | 144.2 |
| 24th Hour | 5.9 | 24.6 | 56.2 |
| 7th Day | | 45.3 | 102.5 |
| White Blood Cell (WBC) Ascorbate Level | | | |
| 4th Hour | −40.5 | 34.1 | 38 |
| 8th Hour | −21.2 | −21.9 | −6.80 |
| 24th Hour | −6.3 | −5.3 | 18.2 |
| 7th Day | | 27.6 | 30.5 |
| 24 Hour Urine Ascorbate | | | |
| % Change | 27.7 | 2760.6 | 486.3 |
| MG/24 Hour | 43.65 | 314.5 | 252 |
| 7th Day Urine Ascorbate | | | |
| % Change | | 4583 | 617 |
| MG/24 Hour | | 459 | 321 |
| 24th Hour Urine Oxalate | | | |
| % Change | 7 | 162 | 35.9 |
| MG/24 Hour | 25.9 | 63.8 | 41.6 |

*increase unless otherwise indicated.

The conclusions which were drawn from this study are:

SERUM ASCORBATE LEVEL

At 4, 8 and 24 hours and 7 days later, test groups had higher serum ascorbate level as compared to both the citrate group and the L-ascorbic group.

WBC ASCORBATE LEVEL

Although all 8th hour WBC ascorbate groups showed an average decrease, test group has the smallest percentage decrease. Four and 24-hour measurement plus the 7th-day level showed that test group was able to maintain the highest white blood cell ascorbate level.

24-HOUR WBC ASCORBATE

24-Hour post various loadings of: citrate, L-ascorbic and test produce similar results. Both the citrate group and L-ascorbic group showed a decrease in WBC ascorbate levels. Test groups maintained a much higher level compared to baseline.

7 DAY POST LOADING OF L-ASCORBIC AND TEST

Average percentage change in WBC Ascorbate is still higher in the Test Group than in the L-ascorbic group.

24-HOUR URINE ASCORBATE OUTPUT

Test groups have less ascorbate output than the citrate and the L-ascorbate groups.

7 DAYS—24 HOUR URINARY ASCORBATE OUTPUT

Test groups have less ascorbate output than the citrate and the L-ascorbate groups.

24-HOUR URINARY OXALATE OUTPUT

Oxalate output is greatly decreased in the test group as compared to the ascorbic group. This means that while taking test produce as a supplement, a person has less chance of forming oxalate-containing kidney calculi than a person taking L-ascorbic.

7 DAY 24-HOUR OXALATE OUTPUT

Prolonged supplementation with test product leads to less excretion of urinary oxalate than supplementation with L-ascorbic.

EXAMPLE 3

To a 2-liter reaction vessel equipped with an agitator and a thermometer is added 30 ml. distilled water and 440 g. (2.5 moles) L-ascorbic acid. To this stirred slurry, finely divided calcium carbonate is added incrementally at a rate such as to produce a constant evolution of carbon dioxide (reaction byproduct), the reaction temperature being maintained is about 20° C. The addition of calcium carbonate is suspended after about 25 g. to 37.5 g. have been added (representing from about 20% to 30% of that required for complete reaction with the L-ascorbic acid charge).

At this point, the temperature is raised to 80° C. Further additions of calcium carbonate are begun, the temperature being maintained in the rage 60° C. to about 70° C. The total quantity of calcium carbonate added is 125 g. (1.25 moles).

The reaction mixture is transferred to a shallow container maintained at a temperature of between 60° C. and 80° C., for a period of from 12 to 36 hours, during which time the pH of the mixture rises to a pH range of 6.0–7.0. At this point, the excess water is removed under vacuum.

The dry products are light tan in color and readily soluble in water, except for unreacted calcium carbonate, to produce neutral solutions.

EXAMPLE 4

Clinical studies using the product of Example 3 yield similar results to those set forth in Example 2.

EXAMPLE 5

The products of Examples 1 and 3 are subjected to qualitative analysis as follows:

After filtering out excess insoluble calcium carbonate, calcium ascorbate was removed from the product by chromatography and the residue was subjected to nuclear magnetic resonance spectroscopy. Likely possibilities for the structures of the components detected by spectroscopy were formulated and these authentic compounds were then synthesized After nmr spectra of these authentic compounds were obtained, they were compared to the nmr spectra of the test specimens. A match of the spectra was used to identify the components of the test specimens.

The techniques employed were 1H and 13C nmr. The aldonic acid salts identified are the calcium salts of L-threonic acid L-xylonic acid and L-lyxonic acid.

EXAMPLE 6

The procedures of Example 1 are repeated except that the reactant added to the ascorbic acid is changed to yield correspondingly different salts of ascorbic acid which are non-toxic and edible in reasonable quantity.

| Reactant | Salt |
| --- | --- |
| sodium bicarbonate | sodium ascorbate |
| magnesium carbonate | magnesium ascorbate |
| potassium bicarbonate | potassium ascorbate |
| zinc oxide | zinc ascorbate |

These products contain the aldonic acid salts corresponding to those identified in Example 5.

EXAMPLE 7

Quantitative analysis of the products of Example 1, 4 and 6 is performed. The products have the indicated compositions:

|  | Wt. % |
| --- | --- |
| Anhydrous metal ascorbate | 80–92 |
| Unreacted metal reagent | 0–7 |
| Dehydroascorbic Acid | 3–9 |
| Moisture | 1.5–4.5 |
| Aldonic Acid Derivatives | 5–6 |

The aldonic acid derivatives include derivatives of the indicated acid in the following approximate proportions in the above residue.

| Acid (Derivative) | Parts by Weight |
| --- | --- |
| Threonic | 8 |
| Xylonic | 3 |
| Lyxonic | 1 |

There are indications that some of one or more of these aldonic acids may be linked to each other or to ascorbates or that ascorbates may be linked.

EXAMPLE 8

Animal feeding studies of the product of Example 1 provide similar results to the human studies of Example 2.

EXAMPLE 9

The procedures of Example 2 are repeated except that the test product is synthesized by mixing reagent grade calcium ascorbate with:

Test A—threonic Acid (calcium salt)
Test B—Xylonic Acid (calcium salt)
Test C—Lyxonic Acid (calcium salt)

in the same weight proportions as the components found in Example 7.

The tests of Example 2 are repeated using these test compounds and using pure calcium ascorbate as an additional control.

These tests confirm that the physiological activity of the mixed ascorbate-aldonic product is due to the aldonic component and that any one of these aldonic components causes the similarly improved absorption and retention of the Vitamin C component.

EXAMPLE 10

This example illustrates the practice of the invention in improving the absorption/retention of aspirin.

Sixteen Wistar derived albino rats, eight male (242–333 gms) and eight female (295–345 gms) were acclimated for seven days prior to beginning this study. During this period the rats were fed Purina(R) Rodent Chow, watered ad lib and housed in self-flushing stainless-steel cages. The animal room was maintained at 70° +/−2° F., 60–80% relative humidity, and had a 12 hr–12 hr light-dark photoperiod.

The rats were randomly assigned to two groups of eight each (4 males and 4 females) and placed in metabolism cages. Group A received U.S.P. aspirin at 54 mg/kg in 2.0 ml distilled water by gavage. Group AM received U.S.P. aspirin at 54 mg/kg plus calcium threonate, (a metabolite of ascorbic acid) at 15 mg/kg in 2.0 ml distilled water by gavage also. Blood samples were taken at 1, 2, 3 and 4 hours after dosing for serum salicylate analysis. Urine was collected if produced at the same time periods for salicylate analysis also. In an effort to maximize urine output the rats were given additional water at 1, 2, 3 and 4 hours by gavage (3 ml).

Blood and urine were collected and analyzed according to the method of Natleson. [Natelson, S. *Techniques of Clinical Chemistry*, ed. 3. p. 649, Charles C. Thomas, Pub. (1971)]. The study was terminated after the 4 hour collection time.

All statistics were calculated via Statistical Analysis System (SAS Institute, Inc., Box 8000, Cary, N.C., 27511) software. The ANOVA (repeated measures model) procedure was used to determine differences in salicylate concentrations between groups.

Figure 1:
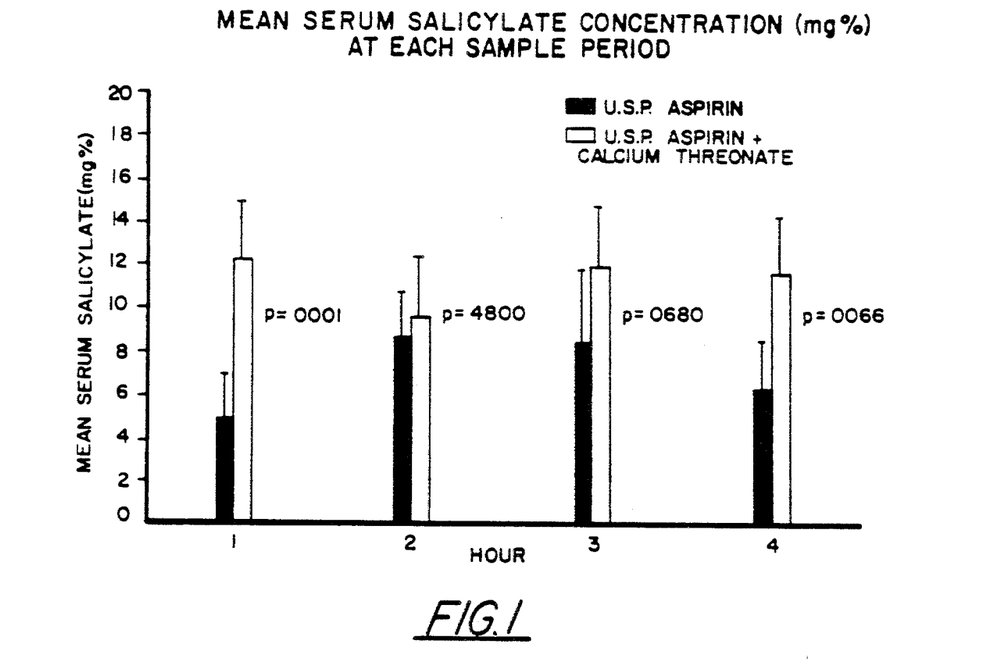
FIG. 1 is a histogram presentation of experimental data depicting the improvement in absorption/retention rate of aspirin, in accordance with the invention.
Figure 2:
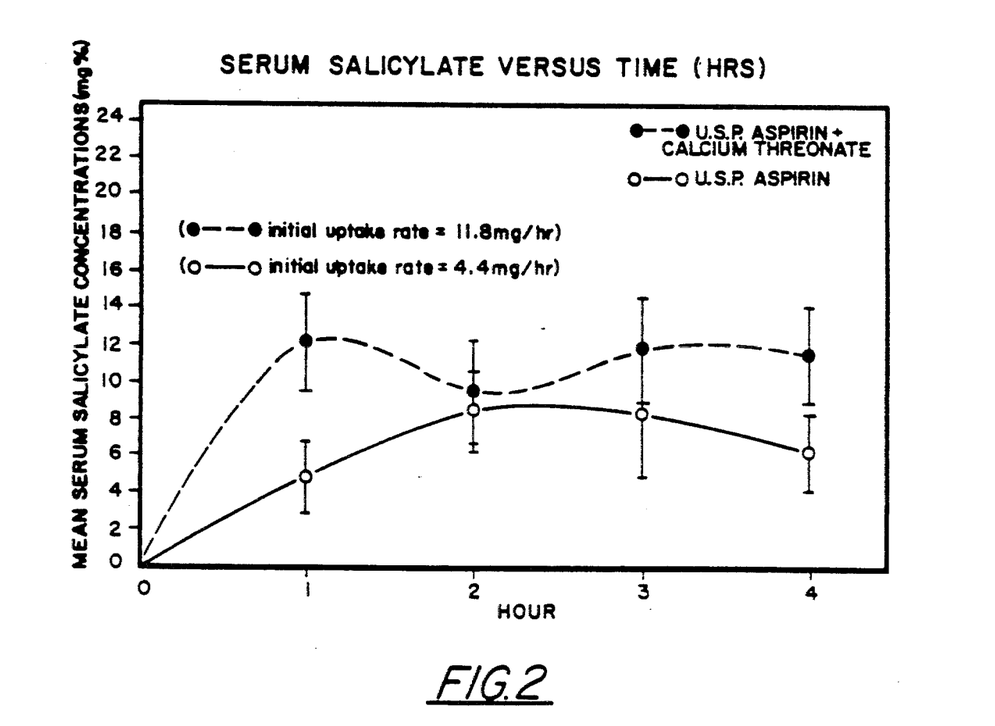
FIG. 2 is a serum salicylate-time profile, illustrating such improvements.

Table 1 shows the actual serum alicylate concentrations for each animal in both Group A and AM, at each sampling time. The average values (X) and standard deviation (SD) for each group and time are given. FIG. 1 is a histogram presentation of the data in Table 1. The significance level (P) of the differences between the two groups at each sample time in salicylate concentration in serum are given next to each set of histograms. FIG. 2 is the serum salicylate profile over time for both groups of rats, standard deviation bars are included. The initial uptake rate (gastrointestinal) is calculated from the linearized curve in the first hour after dosing. Urine salicylate data is not presented in detail but will be discussed below. The groups are not broken down into male and female because there is no significant difference in the serum salicylate related to the sex of the animal.

TABLE 1

INDIVIDUAL ANIMAL SERUM SALICYLATE CONCENTRATIONS (mg %) AT 1, 2, 3 AND 4 HRS OF THE U.S.P. ASPIRIN GROUP (A) AND THE U.S.P. ASPIRIN PLUS ALDONIC GROUP (AM)

| Animal No. | 1 | 2 | 3 | 4 Hrs. |
|---|---|---|---|---|
| GROUP A | | | | |
| 1 | 1.4 | 7.1 | 4.3 | 6.4 |
| 2 | 7.1 | 9.3 | 4.6 | 3.6 |
| 3 | 5.0 | 7.4 | 7.9 | * |
| 4 | 6.7 | 7.4 | 10.7 | * |
| 5 | 3.1 | 6.4 | * | * |
| 6 | 4.0 | * | * | * |
| 7 | 6.7 | 11.4 | 11.1 | 7.1 |
| 8 | 5.7 | 11.4 | 12.1 | 8.6 |
| $\bar{X} \pm$ SD | 4.96 ± 2.00 | 8.63 ± 2.09 | 8.45 ± 3.40 | 6.43 ± 2.10 |
| GROUP AM | | | | |
| 9 | 12.9 | 9.3 | 12.1 | 10.0 |
| 10 | 15.0 | 13.9 | 12.1 | 10.1 |
| 11 | 16.1 | 9.3 | 8.6 | 8.6 |
| 12 | 10.7 | 12.9 | 9.3 | 9.9 |
| 13 | 11.1 | ** | ** | 11.4 |
| 14 | 13.6 | 7.9 | 15.7 | 15.7 |
| 15 | 7.8 | 7.1 | 15.7 | 15.6 |
| 16 | 10.7 | 6.7 | 10.2 | 12.1 |
| $\bar{X} \pm$ SD | 12.24 ± 2.69 | 9.59 ± 2.80 | 11.96 ± 2.87 | 11.68 ± 2.67 |

X = Mean, SD = Standard Deviation
* = Died prior to 4 hours
** = Sample lost in handling It is apparent from the data that the AM group had a much higher initial uptake or absorption of the U.S.P. aspirin. This group had an uptake rate of 11.76 mg/hr., while A group had a much slower uptake rate of 4.40 mg/hr. The AM group curve is biphasic which indicates two processes. The first part of the curve is related to uptake or absorption by the gastrointestinal tract. There is an accelerated uptake in the AM group verses the A group and this is obvious from the respective serum profiles. The second part of the curve is related to the distribution to other body compartments and renal excretion. The difference in the curves at this point (2 hours) is most likely due to decreased salicylate excretion by the kidney in the AM group (U.S.P. Aspirin plus Aldonic). This group appears to be approaching a steady state concentration of salicylate at the higher level than the U.S.P.—aspirin group which is decreasing at this time.

The elimination rate of the two groups differ significantly. The elimination rate of the A group (calculated from the log of the peak) plasma concentration is 1.30 mg/hr., while the AM group is 0.05 mg/hr. This rate of elimination is approximately 26 times greater without the metabolite present.

Urine salicylate analysis shows a trend indicating less salicylate was excreted over time in the AM group relative to the A group. In the first hour after dosing the A group urine was approximately 9.1 mg % and the AM group 5.0 mg %. This is consistent with the higher serum levels in the AM group and lower levels in the A group serum.

The results confirm that the presence of the metabolite increases aspirin absorption initially, acting locally at the gastrointestinal epithelial cells. As the metabolite, itself, becomes absorbed and increases in concentration in the blood it then exerts an inhibitory effect at the kidney. This effect results in the decreased excretion of the aspirin by the renal mechanisms. A lag time is expected until the inhibition of renal excretion is established and this is reflected in the dip in the AM profile at 2 hours. The upswing between 2-3 hours is then due to the inhibition of the renal excretion process and continued absorption.

The increased serum salicylate levels in the AM group are more the result of decreased excretion rather than increased uptake. The AM uptake rate was 2.67 times greater than the A uptake rate. However, the AM elimination rate was 26 times less than the A group. Therefore, the decreased renal excretion had more impact on maintaining serum salicylate levels over time than increased uptake rate.

The foregoing tests demonstrates that the addition of the aldonic compound not only increases the absorption rate of aspirin, but also inhibits the renal organic anion transport system. This results in maintaining aspirin blood levels for a longer period of time by reducing the elimination rate via the secretion process located in the kidney proximal tubules.

EXAMPLE 11

One hundred-eighty dogs of varying breed and age were fed 3 × 30 mgs/kg of the product of Example 1. All of these dogs suffered movement disorders.

The effect of supplementation was measured by changes in the actual symptoms as seen by new clinical evaluation as well as the owner's report on the status of the animal. The effect was measured seven days after supplementation and then again after six weeks. Last evaluation was after more than six months.

GROUPS OF DIAGNOSIS

A number of different ailments were treated, both acute and chronic. In acute illness where symptoms are rapidly changing, one finds it hard to distinguish between the effect of supplementation and other factors. Hence, this test only studied ailments that have a known cause which remains permanent, where the symptoms had been stable over a period of time and where one would assume that they would continue without supplementation.

Animals with the following chronic ailments were chosen: joint-injuries with secondary permanent changes, arthrosis, spondylosis, hip dysplasia, older dico-prolapse with secondary permanent changes, muscle-atrophy as a result of funtio laesa and senile wear-changes in support and motion-systems.

One hundred dogs qualify under the above criteria. Age or breed was not taken into consideration in this report.

TABLE 3

| Number of dogs that showed: | Good improvement/ free of symptoms | Little improvement/ no effect | Total number: |
|---|---|---|---|
| after 1 week | 75 (75%) | 25 (25%) | 100 (100%) |
| after 6 weeks | 79 (79%) | 21 (11%) | 100 (100%) |
| after 6 months | 65 (77.5%) | 20 (22.5%) | 85 (100%) |
| The results with different types of ailments are: | | | |
| Limping and paid caused by hip dysplasia: | | | |
| after 1 week | 32 (72%) | 13 (28%) | 45 (100%) |
| after 6 weeks | 35 (78%) | 10 (22%) | 45 (100%) |
| Spondilosis and back-prolapse: | | | |
| after 1 week | 13 (76.5%) | 4 (23.5%) | 17 (100%) |
| after 6 weeks | 13 (76.5%) | 4 (23.5%) | 17 (100%) |
| Artrosis-changes: | | | |
| after 1 week | 30 (79%) | 8 (21%) | 38 (100%) |

TABLE 3-continued

| Number of dogs that showed: | Good improvement/ free of symptoms | Little improvement/ no effect | Total number: |
|---|---|---|---|
| after 6 weeks | 31 (81.6%) | 7 (18.4%) | 38 (100%) |

This example shows that the product of Example 1 given orally gives symptomatic relief of the pain of chronic deforming changes in the joint and skeleton system in most cases in this group of patients. Neither calcium-ascorbate along nor L-ascorbic acid alone give such relief.

EXAMPLE 12

Ten Wistar derived albino rats, male (375-411 gms), were acclimated for seven days prior to beginning the study. During this period the rats were fed Purina(R) Rodent Chow, watered ad lib and housed in self-flushing stainless-steel cages. The animal room was maintained at 70°±2° F., 60-80% relative humidity, and had a 12 hr-2 hr. light-dark photoperiod.

The rats were randomly assigned to two groups of five each and placed in Nalgene(R) cages. Group A received U.S.P. Piroxican at 0.6 mg/kg, and Group AM received U.S.P. Piroxican at 0.6 mg/kg plus calcium threonate at 15 mg/kg by gavage. Plasma samples were taken at 4, 6, 8 and 10 hours after dosing for plasma Piroxicam analysis.

Selective HPLC was used to analyze Piroxicam and the data analyzed via SAS. The ANOVA repeated measures procedure was used to determine differences in plasma Piroxicam concentrations between groups.

Figure 3:
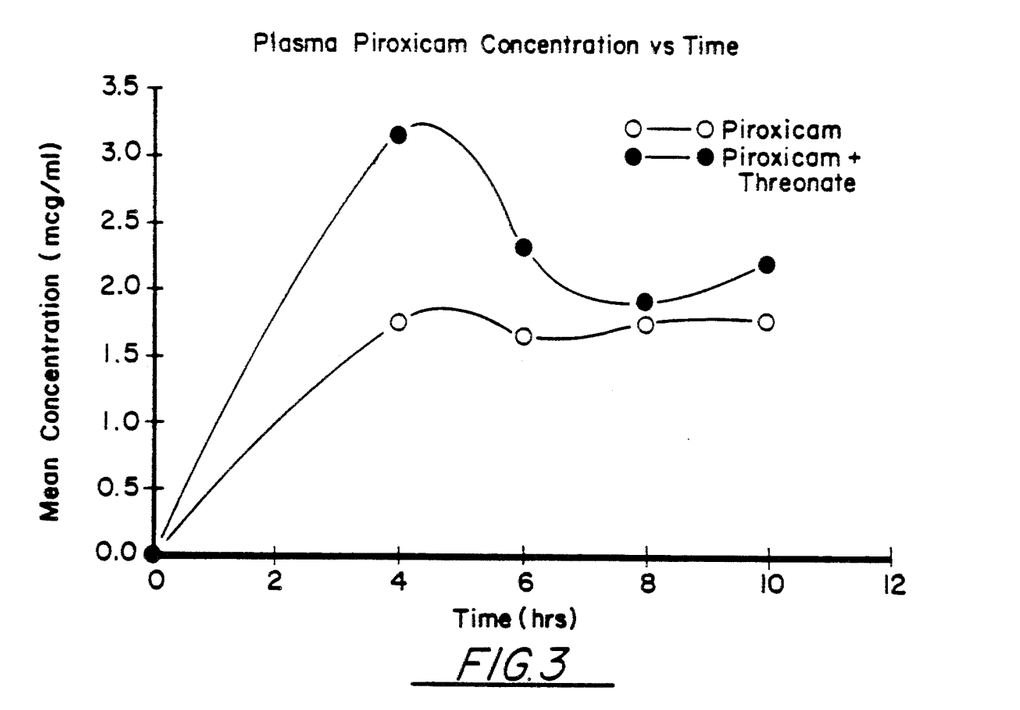
FIG. 3 is a plasma piroxicam-time, profile, depicting improvement in absorption/retention of piroxicam resutling from administering a combination piroxicam-adonic composition.

Table 4 shows the actual plasma concentrations for each animal in Group A and AM at each sampling time. The average values (X) for each group and time are given. FIG. 3 is the plasma profile of the data in Table 4.

The initial rise in plasma levels of Piroxicam is substantially greater in the AM group as compared to the A group. There is a two-fold increase in peak Piroxicam plasma levels in the AM group at 4 hours. These levels begin to fall, thereafter, through the 6 hour point and converge with the A group at 8 hours. However, the AM plasma levels begin to rise again after 8 hours. It appears that there is an effect of the threonate on Piroxicam plasma levels. Statistical differences were found over the 10 hr. period to be p.≦0.07. This is a strong indication that a threonate effect is taking place.

TABLE 4

| Plasma Piroxican Concentration (ug/mL) | | | | |
|---|---|---|---|---|
| | (Hours) | | | |
| Animal No. | 4 | 6 | 8 | 10 |
| Group A | | | | |
| 1 | 2.2 | 2.1 | 1.7 | 2.0 |
| 2 | 1.9 | 1.7 | 1.9 | 1.4 |
| 3 | 1.5 | 1.5 | * | * |
| 4 | 2.1 | 2.0 | 1.8 | 1.7 |
| 5 | 1.1 | 1.0 | 1.6 | 2.0 |
| X | 1.8 | 1.7 | 1.8 | 1.8 |
| Group AM | | | | |
| 6 | 3.1 | 1.2 | 1.4 | 0.9 |
| 7 | 2.2 | 2.0 | 1.8 | 1.6 |
| 8 | 5.9 | 4.8 | 3.1 | 5.6 |
| 9 | 1.3 | 1.0 | 0.8 | 0.6 |
| 10 | 3.3 | 2.7 | 2.5 | 2.3 |

TABLE 4-continued

| Plasma Piroxican Concentration (ug/mL) | | | | |
|---|---|---|---|---|
| | (Hours) | | | |
| Animal No. | 4 | 6 | 8 | 10 |
| X | 3.2 | 2.3 | 1.9 | 2.2 |

Group A -- U.S.P. piroxicam (0.6 mg/kg)
Group AM -- U.S.P. piroxicam (0.6 mg/kg), threonate (15 mg/kg)
* died during study

EXAMPLE 13

Ten Wistar derived Albino rats, male (420-456 gms), were acclimated for seven days prior to beginning the study. During this period the rats were fed Purina(R) Rodent Chow, watered ad lib and housed in self-flushing stainless-steel cages. The animal room was maintained at 70°±2° F., 60-80% relative humidity, and had a 12 hr-12 hr light-dark photoperiod.

The rats were randomly assigned to two groups of five each. Group A rats were gavaged daily for 3 days with 1.0 ml distilled water prior to beginning the study. Group AM rats were gavaged daily with 15 mg/kg/ml of calcium threonate for 3 days also. Threonate dosages were corrected for increases in body weights daily in insure the 15 mg/kg dose was maintained.

On day 4 the Group A rats were gavaged with Piroxicam at 0.6 mg/kg and group AM rats with 0.6 mg/kg Piroxicam and 15 mg/kg threonate. Plasma samples were taken at 4, 6, 8 and 10 hrs. post-dosing for plasma Piroxicam analysis.

Selective HPLC was used to analyze Piroxicam. The data was analyzed statistically by the SAS procedure. The ANOVA repeated measures procedure was used to determine differences in plasma Piroxicam concentration between groups.

Figure 4:
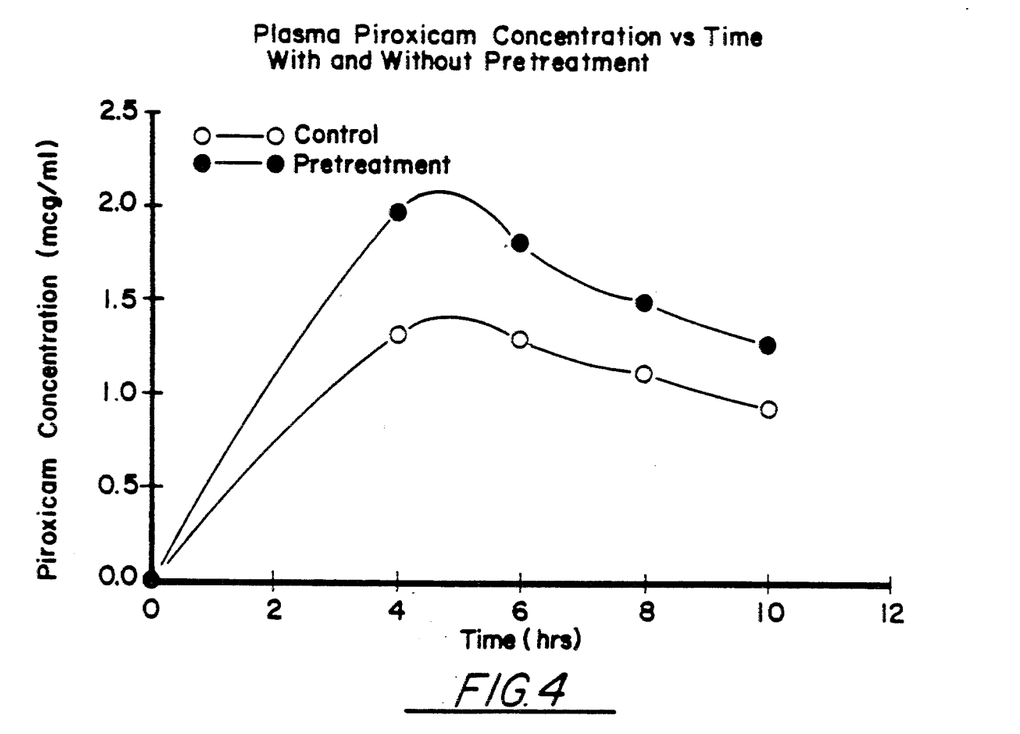
FIG. 4 is a similar plasma piroxicam-time profile depicting the improvement in absorption/retention of piroxicam resulting from sequential administration of the aldonic and piroxicam components.

Table 5 shows the actual plasma Piroxicam concentrations for each animal in Group A and AM (metabolite pretreatment). The average (X) values for each group at each time period are given. FIG. 4 is the plasma profile constructed from the data given in Table 5.

It is apparent from the plasma profiles that the AM pretreatment group had significantly higher Piroxicam plasma levels than the non-treatment group. The AM group had a higher uptake rate and maintained higher plasma levels over the ten-hour period. The difference averages about 60% higher plasma levels in the AM group. These higher levels are statistically significant at p.≦0.05).

Pretreatment with calcium theonate significantly increased and maintained the plasma levels of Piroxicam (Feldene) over a ten-hour period.

TABLE 5

| Piroxicam Plasma Concentration (ug/mL) | | | | |
|---|---|---|---|---|
| Animal No. | 4 | 6 | 8 | 10 |
| Group A | | | | |
| 1 | 2.1 | 1.8 | 1.7 | 1.4 |
| 2 | 1.1 | 1.0 | 0.8 | 0.6 |
| 3 | 1.5 | 1.4 | 1.3 | 1.1 |
| 4 | 0.8 | 0.7 | 0.7 | 0.6 |
| 5 | 1.1 | 1.6 | 1.1 | 1.0 |
| X | 1.3 | 1.3 | 1.1 | 0.9 |
| Group AM | | | | |
| 6 | 2.4 | 2.3 | 1.7 | 1.4 |
| 7 | 2.2 | 1.7 | 1.6 | 1.7 |
| 8 | 2.0 | 1.7 | 1.9 | 1.5 |
| 9 | 1.9 | 2.3 | 1.4 | 1.0 |
| 10 | 1.4 | 1.1 | 0.9 | 0.8 |

TABLE 5-continued

| | Piroxicam Plasma Concentration (ug/mL) | | | |
|---|---|---|---|---|
| Animal No. | 4 | 6 | 8 | 10 |
| X | 1.9 | 1.8 | 1.5 | 1.2 |

Group A (no pretreatment), Day 4—0.6 mg/kg U.S.P. Piroxicam
Group AM (pretreatment), Day 1-3--15 mg/kg metabolite; Day 4—0.6 mg/kg U.S.P. Piroxicam; 15 mg/kg threonate

EXAMPLE 14

25 cm$^2$ T-flasks containing 3T3 mouse fibroblasts were incubated with 100 mg % (1 mg/mL) calcium L-threonate (pH 7.4) for hour at 37° C. A control group was incubated with Riner's as a control.

The incubation fluid was removed and 1.25 mg % ascorbic acid was added to each flask. (5 ul of 14C-L ascorbic acid was added, 10.0 mCi/mmol, 0.05 mCi/ml). The pH was adjusted to 7.62 and the flasks were maintained at 37° C. for 20 minutes.

The flasks were then washed with 4 ml HBSS(−) and then were trypsinized with 0.1 ml trypsin-EDTA for 5 minutes. The cells were resuspended in 4 ml ice cold HBSS(−) to stop the enzymatic reaction. The cells were centrifuged for 10 minutes at 1000 G. The cells were then washed and resuspended in 4 ml HBSS(−). The cells were again centrifuged (10 min, 1000 G), resuspended in 1.0 ml distilled H$_2$O and sonicated for 90 seconds.

0.5 ml of each sample was used for counting $^{14}$C and 0.5 ml was used for protein analysis using the Bradford method.

The uptake of $^{14}$C into the cells was calculated, yielding the following results:

TABLE 6

| | Flask # | DPM/ug | Uptake Ratio |
|---|---|---|---|
| Calcium-L- | 3.5.15 | 0.835 | 1.30 |
| Threonate | 3.5.5 | 1.341 | 2.09 |
| | 3.5.1 | 1.384 | 2.16 |
| Control | 3.5.10 | 0.697 | 1.09 |
| | 3.5.7 | 0.626 | 0.976 |
| | 3.5.8 | 0.601 | 0.937 |
| average (Calcium L-Threonate) | = | 1.19 | 1.86 |
| average (Ringer's) | = | 0.641 | 1.00 |

Figure 5:
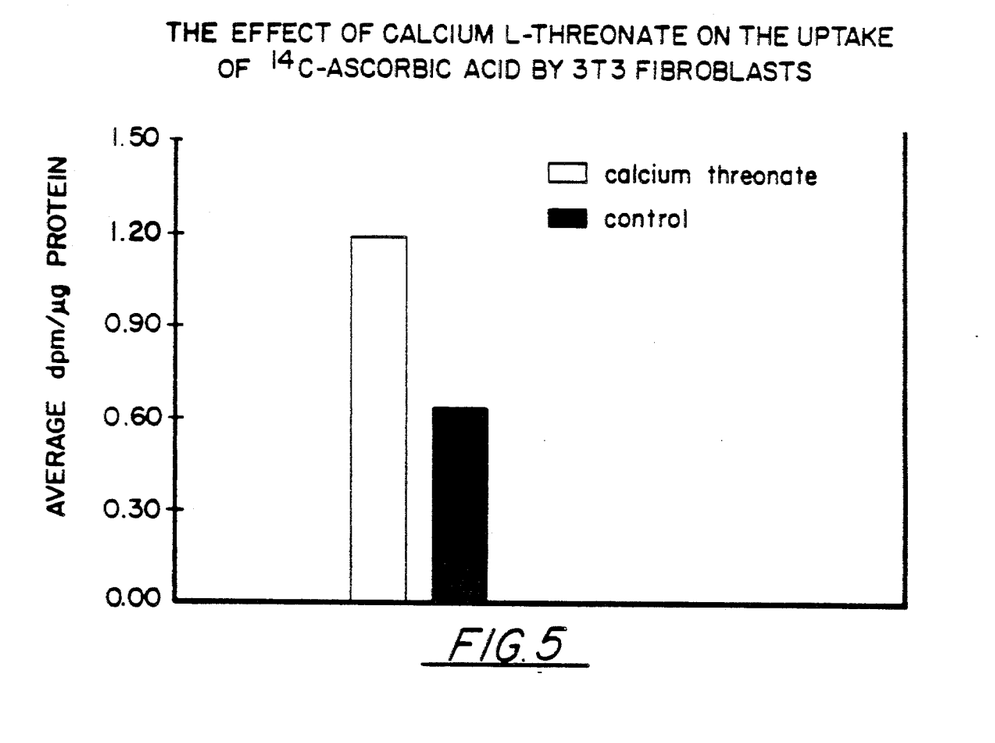
FIG. 5 depicts the improved uptake of ascorbic acid by 3T3 fibroblasts resulting from inclusion of the aldonic component.

Thus the uptake of $^{14}$C-L-ascorbic acid was 1.86 times greater in the cells from the flasks containing the threonate than the cells containing the control solution. These results are statistically significant (Stutent's T-test, alpha=0.05). These results are shown graphically in FIG. 5.

Having described my invention in such terms as to enable those skilled in the art to which it pertains to understand and practice, and having described the presently preferred embodiments thereof,

I claim:

1. A therapeutic composition, said composition comprising:
   (a) an effective amount of a therapeutically active compound, said compound having
      (i) a molecular weight below about 5,000,
      (ii) an acidic functional group and a pKa of ≦6 at physiological pH=7.4, and
      (iii) which is normally eliminated unmetabolized via the renal tubular secretion pathway for or- and ganic anions;
   (b) at least one compound selected from the group consisting of L-threonic, L-xylonic and L-lyxonic acids, and the edible non-toxic salts, aldono-lactones and aldono-lactides thereof, in an amount effective to increase the body absorption rate of said active compound.

2. The composition of claim 1 wherein said active compound is piroxicam.

3. The composition of claim 1 in which said active compound is aspirin.

4. The composition of claim 1 in which said compound of subparagraph (b) is present in an amount effective to reduce the body elimination rate of said active compound.

5. A Vitamin C composition, said composition comprising:
   (a) an effective amount of a compound having Vitamin C activity, selected from the group consisting of (i) dehydroascorbic acid, (ii) L-ascorbic acid and the edible salts thereof; and
   (b) at least one compound selected from the group consisting of the aldono-lactones of L-threonic acid, L-xylonic acid, L-lyxonic acid and the edible salts of L-threonic acid, L-xyonic acid and L-lyxonic acids, in an amount effective to increase the human body absorption rate of said Vitamin C compound.

6. The composition of claim 5 in which the amount of aldonic compound is effective to increase the absorption rate of said Vitamin C compound.

7. The composition of claim 5 in which the amount of aldonic compound is effective to decrease the excretion rate of said Vitamin C compound.

8. A method for improving the effectiveness of a therapeutically active compound, said compound having
   a molecular weight below about 5,000,
   an acid functional group and a pKa of ≦6 at physiological pH=7.4, and
   which is normally eliminated unmetabolized via the renal tubular secretion pathway for organic anions,
said method consisting of the step of administering to a subject an effective dose of a composition comprising:
   (a) an effective amount of a therapeutically active compound; and
   (b) at least one compound selected from the group consisting of L-threonic acid, L-lyxonic acids, and the edible non-toxic salts, aldono-lactones and aldono-lactides thereat, in an amount effective to increase the body absorption rate of said active compound.

9. The method of claim 8 in which said active compound is piroxicam.

10. The method of claim 8 in which said active compound is aspirin.

11. The method of claim 8 in which the compound of subparagraph (b) is present in an amount effective to reduce the body elimination rate of said active compound.

12. A treatment method for improving the effectiveness of a therapeutically active compound, said compound having
   a molecular weight below about 5,000,
   an acidic functional group and a pKa of ≦6 at physiological pH=7.4, and
   which is normally eliminated unmetabolized via the renal tubular secretion pathway for organic anions,
said method comprising, in sequence, the step of:

(a) administering to a subject at least one compound selected from the group consisting of L-threonic, L-xylonic and L-lyxonic acids, and the edible non-toxic salts, aldono-lactones and aldono-lactides thereof to establish a concentration thereof in the subject in an amount sufficient to improve the effectiveness of said active compound; and (b) thereafter administering to said subject the composition of claim 1.

13. The method of claim 12 in which said active compound is piroxicam.

14. The method of claim 12 in which the compound of subparagraph (a) is administered in an amount to establish a concentration thereof in the subject effective to reduce the body elimination rate of said active compound.

15. A method for establishing high Vitamin C levels in the human body which comprise the step of orally administering to a subject an effective amount of the composition of claim 5.

16. The method of claim 15 in which the amount of aldonic compound is affective to increase the absorption rate of said Vitamin C compound.

17. The method of claim 15 in which the amount of aldonic compound is effective to decrease the excretion rate of said Vitamin C compound.

18. A method of suppressing the excretion of organic anions via the renal tubular secretion pathway comprising the step of establishing an effective blood concentration of a compound selected from the group consisting of L-threonic, L-xylonic and L-lyxonic acids, and the edible non-toxic salts, aldono-lactones and aldono-lactides thereof.

19. A method of improving the absorption of organic anions in body tissue comprising the step of establishing an effective blood concentration of a compound selected from the groups consisting of L-threonic, L-xylonic and L-lyxonic acids, and the edible non-toxic salts, aldon-lactones and aldon-lactides thereof.

* * * * *

UNITED STATES PATENT AND TRADEMARK OFFICE
CERTIFICATE OF CORRECTION

PATENT NO. : 5,070,085
DATED : December 3, 1991
INVENTOR(S) : Richard G. Markham It is certified that error appears in the above-identified patent and that said Letters Patent is hereby corrected as shown below:

On the title page, item [*], please delete "The portion of the term of this patent subsequent to April 18, 2006 has been disclaimed." and insert "The term of this patent shall not extend beyond the expiration date of U.S. Patent No. 4,822,816 or U.S. Patent No. 4,968,716."

Signed and Sealed this

Eleventh Day of April, 2000

Attest:

Q. TODD DICKINSON

Attesting Officer

Director of Patents and Trademarks